(12) United States Patent
Winsauer et al.

(10) Patent No.: US 8,257,078 B2
(45) Date of Patent: Sep. 4, 2012

(54) ORTHODONTIC CORRECTIVE APPLIANCE, ESPECIALLY FOR CORRECTING MALPOSITIONED MOLARS

(75) Inventors: Heinz Winsauer, Bregenz (AT); Hartwig Ahnfeldt, Siegen (DE)

(73) Assignees: Heinz Winsauer, Bregenz (AT); Promedia A. Ahnfeldt GmbH, Siegen (DE)

( * ) Notice: Subject to any disclaimer, the term of this patent is extended or adjusted under 35 U.S.C. 154(b) by 0 days.

(21) Appl. No.: 13/234,708

(22) Filed: Sep. 16, 2011

(65) Prior Publication Data

US 2012/0003600 A1    Jan. 5, 2012

Related U.S. Application Data

(62) Division of application No. 12/455,578, filed on Jun. 3, 2009.

(30) Foreign Application Priority Data

Jun. 5, 2008  (DE) .................... 20 2008 007 527 U

(51) Int. Cl.
  *A61C 3/00*  (2006.01)
(52) U.S. Cl. .......................................................... 433/7
(58) Field of Classification Search .................. 433/6, 7, 433/18, 19, 21, 24
See application file for complete search history.

(56) References Cited

U.S. PATENT DOCUMENTS

| 3,460,253 | A | 8/1969 | Cammarata |
| 5,785,520 | A | 7/1998 | Carano et al. |
| 6,358,046 | B1 | 3/2002 | Brehm et al. |
| 6,964,566 | B2 | 11/2005 | Sapian |
| 2003/0091952 | A1 | 5/2003 | Bowman et al. |

FOREIGN PATENT DOCUMENTS

| DE | 20015992 | 3/2001 |
| WO | 2008041120 | 4/2008 |

*Primary Examiner* — Cris L Rodriguez
*Assistant Examiner* — Eric Rosen
(74) *Attorney, Agent, or Firm* — Lucas & Mercanti, LLP; Klaus P. Stoffel

(57) ABSTRACT

An orthodontic corrective appliance for correcting malpositioned molars, wherein one end of the appliance is mounted on a supporting device, and the other end is applied to the given molar with spring loading includes a pusher element which is guided axially in a sleeve and is acted upon by a compression spring, and the free end of the pusher element extends from the sleeve and is provided with a connecting piece which is applied to the supporting device. Several small tubes on the outer surface of the sleeve have inner bores that guide and support a spacer bar that extends parallel to the sleeve. The end of the spacer bar that points towards the connecting piece is supported on one of the tubes, and the end of the spacer bar that faces away from the connecting piece is supported on a transpalatal arch, a Goshgarian lock or similar element.

4 Claims, 4 Drawing Sheets

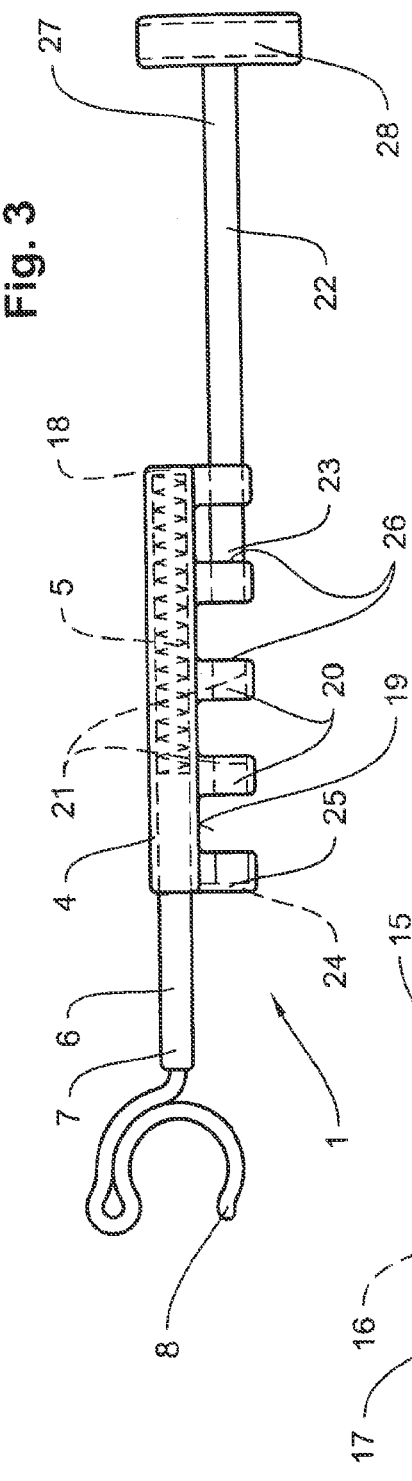

Fig. 5
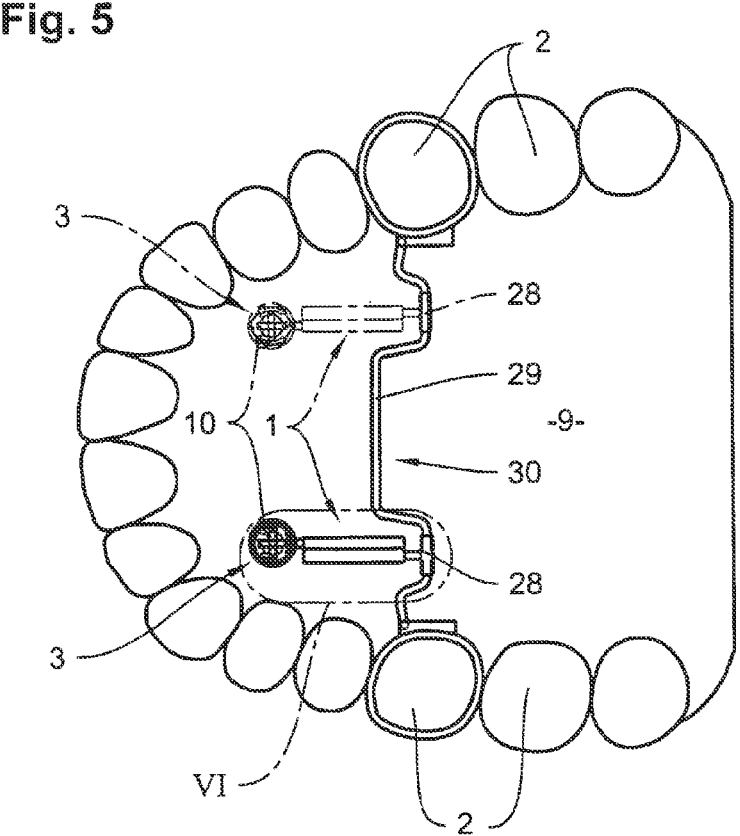
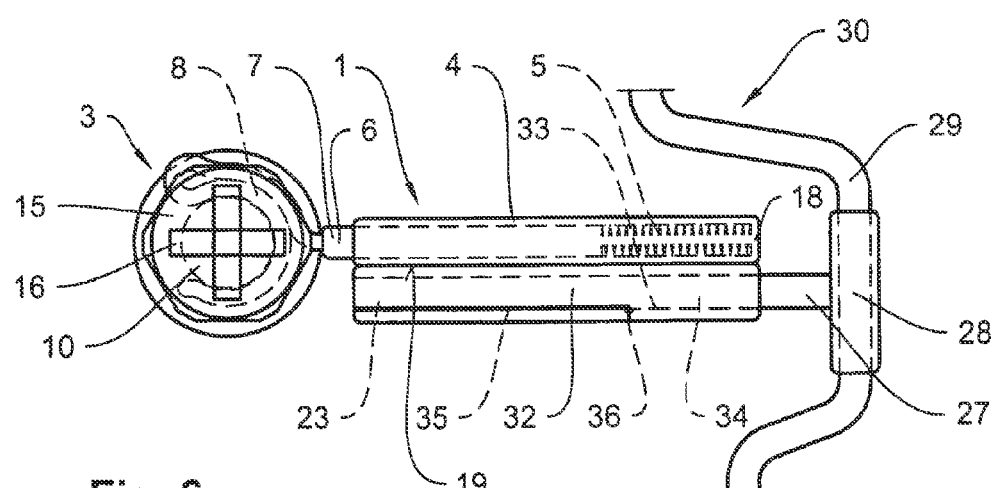
Fig. 6

ORTHODONTIC CORRECTIVE APPLIANCE, ESPECIALLY FOR CORRECTING MALPOSITIONED MOLARS

CROSS-REFERENCE TO RELATED APPLICATIONS

The present application is a Divisional Application of U.S. patent application Ser. No. 12/455,578, filed Jun. 3, 2009, which claims priority of DE 20 2008 007 527.0, filed Jun. 5, 2008, the priority of these application is hereby claimed and these applications are incorporated herein by reference.

BACKGROUND OF THE INVENTION

The present invention relates to an orthodontic corrective appliance, especially for correcting malpositioned molars, such that one end of the appliance is mounted on a supporting device, and the other end is applied to the given molar with spring loading.

Malpositioning of molars is already evident from the presence of crowded teeth in the area of the incisors and their neighboring teeth. To correct this, it is necessary to correct the malpositioning of the given molar, i.e., the molar must be correctly aligned or pushed to the rear, which then allows the malpositioning aligned tooth or teeth to move into their proper positions.

To this end, U.S. Pat. No. 5,785,520 describes an orthodontic distalizing appliance with a supporting framework. This appliance also has a device for anchoring the framework on at least one anchoring tooth and spring-loaded pusher elements. The pusher elements are interposed between the framework and a device for fastening to another tooth of at least one side of the arch. The pusher elements exert a distalizing force in the direction of the longitudinal axis of the arch in the area of the tooth that is being distalized. The pusher elements are arranged on the lingual side of the dental arch, preferably in a position more towards the basal gingiva and underlying bony support of the arch.

However, this appliance has the disadvantage that the present tooth situation is endangered by the mounting of the supporting framework on the anchoring tooth or teeth and the mounting of the pusher elements connected with the supporting framework. Moreover, a readjustment of the spring-loaded pusher elements seems very complicated, and the displacement of the pusher elements is very limited.

SUMMARY OF THE INVENTION

Therefore, it is the primary object of the invention to create an appliance of the general type described above, which has a relatively simple design with which a readjustment of the elastic displacement can be accomplished in a very simple way, which allows a relatively large distance, and with which the tooth situation of unaffected teeth is not endangered.

In accordance with the invention, this object is achieved by an appliance which includes a pusher element, which is guided axially in a first sleeve and is acted upon by a compression spring; wherein a free end of the pusher element extends from the sleeve and is provided with a connecting piece, which is applied to the supporting device which is comprised of an anchor screw that is configured to be screwed into the given jaw; wherein a second sleeve is installed on an outer surface of the first sleeve, the first sleeve having inner bores in which a spacer bar, which extends parallel to the sleeve, is guided and supported; wherein, depending on the required extraction length of the spacer bar, which has toothing that extends over a portion of its length, the end of the spacer bar that is directed towards the connecting piece is supported in barb-like fashion by the toothing on at least one notch of the second sleeve; and where the end of the spacer bar that faces away from the connecting piece is supported on a transpalatal arch, a Goshgarian lock or similar element.

The appliance of the invention is characterized, above all, by the fact that the position of unaffected teeth is not endangered by the use of anchor screws screwed into the jaw, because no pressure whatsoever is exerted on the other teeth. A readjustment of the elastic displacement is possible with relatively simple means, and the adjustable distance is significantly greater than in conventional appliances.

The various features of novelty which characterize the invention are pointed out with particularity in the claims annexed to and forming a part of the disclosure. For a better understanding of the invention, its operating advantages, specific objects attained by its use, reference should be had to the drawings and descriptive matter in which there are illustrated and described preferred embodiments of the invention.

BRIEF DESCRIPTION OF THE DRAWING

In the drawing:

FIG. 3 is an enlarged top view of the appliance according to FIG. 1 with the pusher element extended and the spacer bar pulled out.

FIG. 4 is an enlarged side view of the supporting device with the anchor screw and with the pusher element or compression bar clipped on.

FIG. 5 is a top view of a maxilla with a second embodiment of an appliance.

FIG. 6 shows an enlarged segment VI from FIG. 5, in which the appliance is shown with the pusher element pretensioned and the spacer bar retracted.

FIG. 7 is an enlarged top view of the appliance according to FIG. 5 with the pusher element extended and the spacer bar pulled out.

FIG. 8 is an enlarged side view of another embodiment of the appliance, in which the appliance is shown with the pusher element pretensioned with the connecting piece rotated 90° and the spacer bar is retracted and is offset at an end opposite the connecting piece, wherein the offset end of the spacer bar acts on a Goshgarian lock.

DETAILED DESCRIPTION OF THE INVENTION

Figure 1:
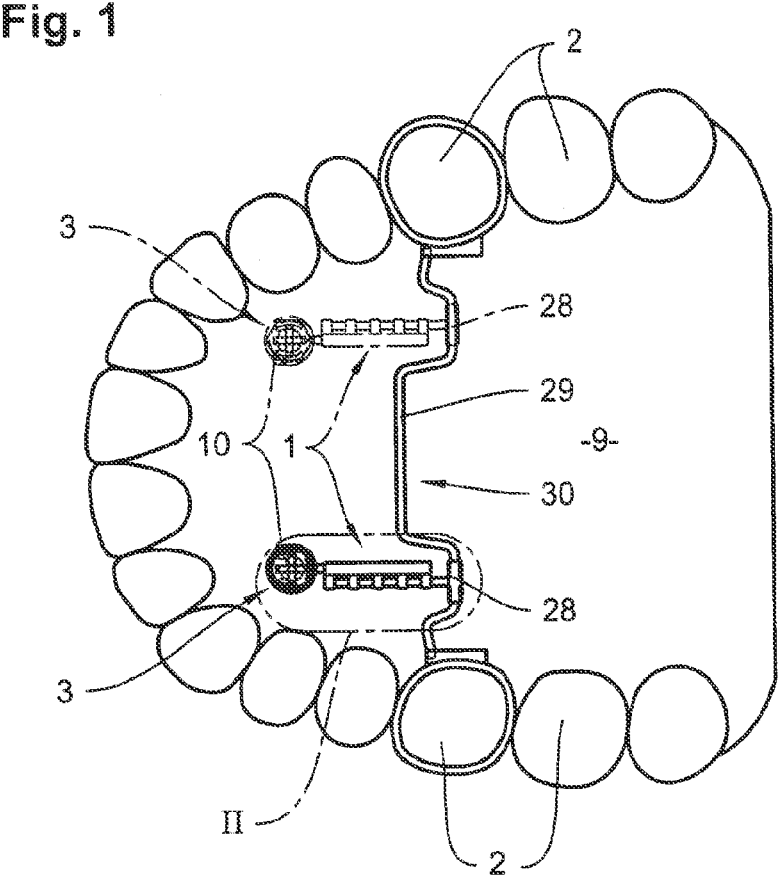
FIG. 1 is a top view of a maxilla with a first embodiment of an appliance.

The appliances 1 illustrated in the drawings are orthodontic corrective appliances, especially for the correction of malpositioned molars 2. One end of the appliance 1 is mounted on a supporting device 3, and the other end is applied to the given molar 2 with spring loading.

All of the appliances 1 include a pusher element 6, which is guided axially in a sleeve 4 and is acted upon by a compression spring 5. The free end 7 of the pusher element 6 extends from the sleeve 4 and is provided with a connecting piece 8, which is applied to the supporting device 3, which consists of an anchor screw 10 that preferably can be screwed into the given jaw 9 (see especially FIGS. 4 and 8).

The head portion 12 of the anchor screw 10 adjacent to the threaded shaft 11 (FIGS. 4 and 8) can consist, for example, of a collar 13 and a screw head 15, which is separated from the collar 13 by a shank 14 that is recessed from the collar 13.

The screw head 15 preferably has Phillips slots. In addition, the screw head 15 can have a polygonal outer periphery (hexagonal in the present case), with which the anchor screw 10 can be screwed into the jaw 9. Naturally, the anchor screw 10 can also be screwed into the jaw 9 by using the Phillips slots 16 provided in the screw head 15.

The compression spring 5, which is preferably made of Nitinol, is supported at one end on a wall 18 that seals the sleeve 4 and at the other end on the pusher element 6. The connecting piece 8 of the pusher element 6 is preferably designed in the form of a clip, such that the connecting piece 8 acts on and is held on the shank 14 of the anchor screw 10 by positive locking and frictional locking.

To obtain an angularly stable connection, the connection of the pusher element 6 with its connecting piece 8 acting on the shank 14 can, if necessary, be additionally fixed by a curing adhesive or plastic. To this end, it is preferred that the space between the screw head 15 and the collar 13 be filled with the plastic.

Instead of fixing with plastic, it is also possible, if necessary, for the connecting piece 8 of the pusher element 6 that acts on the shank 14 to be compressed by the pusher element 6.

Alternatively, the connecting piece 8 can also be formed as a straight or bent wire end (not shown), which, for example, is inserted in a bore (also not shown) in the screw head 15 and, if necessary, secured there. It would also be perfectly possible to construct the connecting piece 8 as a closed ring (not shown) that would have to be placed over the screw head 15.

Figure 2:
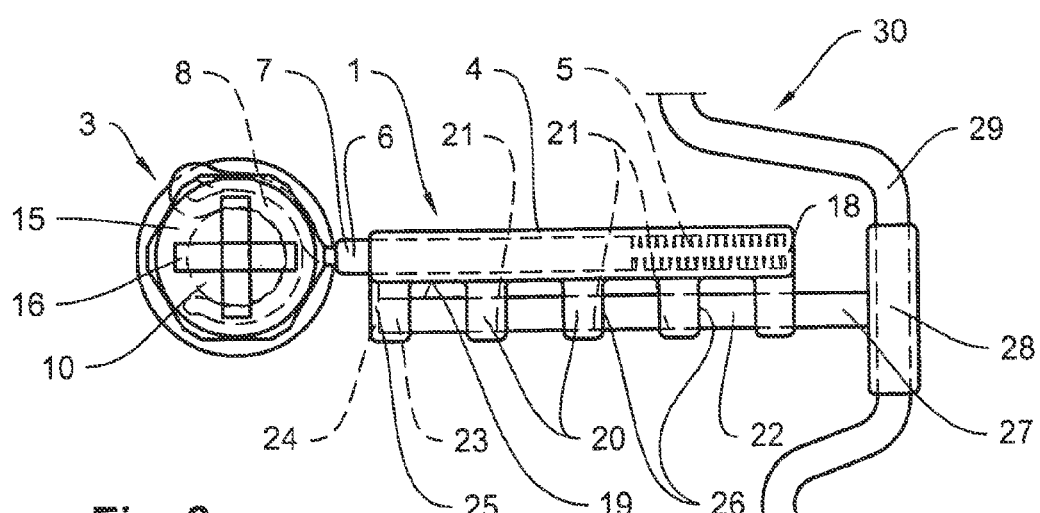
FIG. 2 shows an enlarged segment II from FIG. 1, in which the appliance is shown with the pusher element pretensioned and the spacer bar retracted.

In the specific embodiments illustrated in FIGS. 1 to 3 and FIG. 8, several small tubes 20 are provided on the outer surface 19 of the sleeve 4. The tubes 20 are uniformly distributed one after the other along the length of the sleeve 4 and have inner bores 21 that guide and support a spacer bar 22 that extends parallel to the sleeve 4. The end 23 of the spacer bar 22 that points towards the connecting piece 8 is supported on one of the tubes 20, depending on the required extraction length of the spacer bar 22.

When the appliance 1 is pushed together, the spacer bar 22 is supported on the end wall 24 on the side 25 (which faces the connecting piece 8) of the tube 20 that is situated closest to the connecting piece 8, and when the appliance 1 is pulled apart, the spacer bar 22 is supported on the sides 26 (which face away from the connecting piece 8) of the tubes 20 after the latter have been compressed with pliers or the like. Preferably, the ends of the small tubes 20 that face away from the sleeve 4 are slotted for this purpose. Naturally, the tube 20 on which the spacer bar 22 is supported depends on the required extraction length.

In the embodiments illustrated in FIGS. 1 to 3 and FIGS. 5 to 7, a connecting tube 28 that extends transversely to the spacer bar 22 can be mounted on the end 27 of the spacer bar 22 that faces away from the connecting piece 8, and, e.g., the wire 29 of a transpalatal arch 30 arranged between two opposite molars 2 extends through this connecting tube 28. Naturally, as FIG. 8 shows, in all of the embodiments, the spacer bar 22 can also be applied directly to a Goshgarian lock 31 or similar element mounted on the given molar 2. In this case, the connecting tube 28 that extends transversely to the spacer bar 22 is eliminated.

Figures 7, 8:
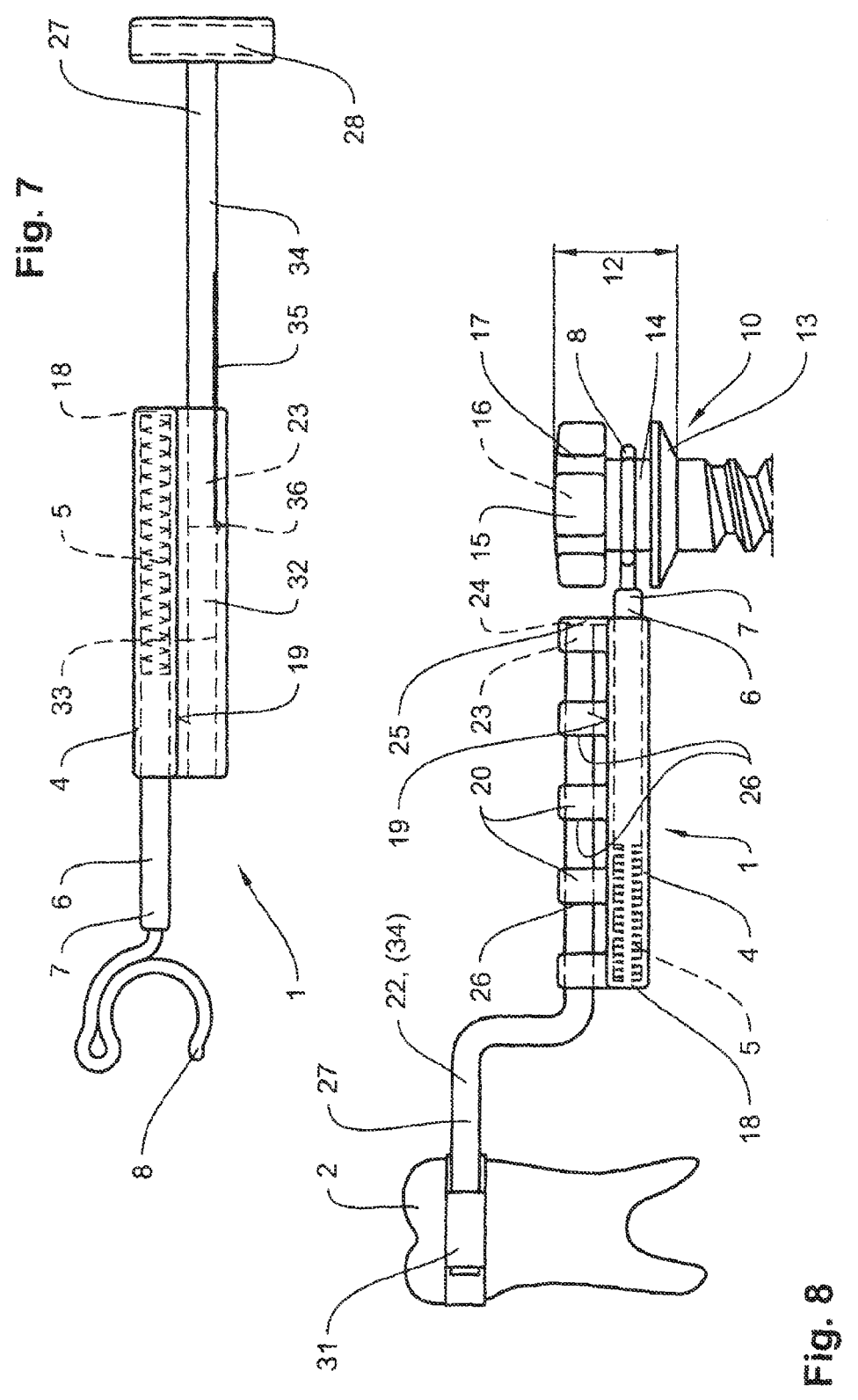

In the embodiment shown in FIGS. 5 to 7, instead of the small tubes 20 on the outer surface 19 of the sleeve 4, another sleeve 32 is installed, in whose inner bores 33 a spacer bar 34, which likewise extends parallel to the sleeve 4, is guided and supported. Depending on the required extraction length of the spacer bar 34, which has toothing 35 that extends over a portion of its length, the end 23 of the spacer bar 34 that is directed towards the connecting piece 8 is supported in barb-like fashion by the toothing 35 on at least one notch 36 of the additional sleeve 32.

As a result of the appliance 1 being supported on the supporting device 3 at one end and on the transpalatal arch 30 or on the Goshgarian lock 31 or similar element at the other end, the spring-loaded pusher element 6 exerts pressure on the given molar 2 that is to be aligned or shifted. To this end, the appliance 1 is mounted on the side of the jaw 9 on which is located the molar 2 that is to be aligned or shifted. If it is necessary to align or shift molars 2 on both sides of the jaw 9, an appliance 1 must be provided on each side of the jaw 9 (In FIGS. 1 and 5, the second appliance 1 is indicated by a dot-dash line.).

These embodiments of the appliance 1 of the invention allow relatively simple alignment or shifting of molars 2. Readjustment takes place automatically at first by means of the spring-loaded pusher element 6. Only after the end of the spring excursion has been reached does it become necessary for the dentist to intervene. He then pulls out the spacer bar 22, 34 sufficiently far in the direction of the transpalatal arch 30 or the Goshgarian lock 31 or similar element and causes it to lock in place by squeezing the small tube 20 located behind the end 23 of the spacer bar 22 that is directed towards the connecting piece 8 or causes it to automatically lock by means of the engagement of the toothing 35 with the notch 36, so that the compression spring 5 is again prestressed and can again exert pressure on the given molar 2.

The form of the connecting piece 8 illustrated in the drawings is to be seen merely as an example. Naturally, the connecting piece 8 can take various other forms, for example, the form of a clip, ring, rod or the like, which acts on and is held on the supporting device 3 or the anchor screw 10.

While specific embodiments of the invention have been shown and described in detail to illustrate the inventive principles, it will be understood that the invention may be embodied otherwise without departing from such principles.

We claim:

1. An orthodontic corrective appliance, for correcting malpositioned molars, comprising: a supporting device comprised of an anchor screw configured to be screwed into a given jaw, one end of the appliance being mounted on the supporting device, and any other end being configured to be applied to a given molar with spring loading; a first sleeve; a pusher element guided axially in the first sleeve; and a compression spring arranged to act on the pusher element; wherein a free end of the pusher element extends from the first sleeve; a connecting piece provided at the free end of the pusher element, the connecting piece being applied to the supporting device; a second sleeve installed on an outer surface of the first sleeve, the second sleeve having inner bores; and a spacer bar, which extends parallel to the second sleeve; wherein the inner bores of the second sleeve guide and support the space bar; wherein, depending on a required extraction length of the spacer bar, which has toothing that extends over a portion of a length of the spacer bar, an end of the spacer bar that is directed towards the connecting piece is supported on at least one notch of the second sleeve by the toothing; and where an end of the spacer bar that faces away from the connecting piece is configured to be supported on a transpalatal arch or a lock element.

2. An appliance in accordance with claim 1, further comprising a connecting tube that extends transversely to the spacer bar and is mounted on the end of the spacer bar that faces away from the connecting piece, and wherein a wire of the transpalatal arch arranged between two opposite molars is configured to extend through the connecting tube.

3. An appliance in accordance with claim 1, wherein the compression spring is made of Nitinol.

4. An appliance in accordance with claim 1, wherein the connecting piece is formed as a clip, such that the connecting piece acts on a shank of the anchor screw by positive locking and frictional locking.

* * * * *